United States Patent
Hashimoto et al.

(10) Patent No.: US 9,572,520 B2
(45) Date of Patent: Feb. 21, 2017

(54) MOVEMENT ASSISTANCE DEVICE, AND SYNCHRONY BASED CONTROL METHOD FOR MOVEMENT ASSISTANCE DEVICE

(71) Applicant: SHINSHU UNIVERSITY, Nagano (JP)

(72) Inventors: Minoru Hashimoto, Nagano (JP); Yasuhiro Wakui, Nagano (JP)

(73) Assignee: SHINSHU UNIVERSITY, Nagano (JP)

(*) Notice: Subject to any disclaimer, the term of this patent is extended or adjusted under 35 U.S.C. 154(b) by 292 days.

(21) Appl. No.: 14/367,393

(22) PCT Filed: Dec. 21, 2012

(86) PCT No.: PCT/JP2012/083326
§ 371 (c)(1),
(2) Date: Jun. 20, 2014

(87) PCT Pub. No.: WO2013/094747
PCT Pub. Date: Jun. 27, 2013

(65) Prior Publication Data
US 2015/0327796 A1    Nov. 19, 2015

(30) Foreign Application Priority Data

Dec. 21, 2011 (JP) .................. 2011-279362

(51) Int. Cl.
*A61H 1/00* (2006.01)
*A61B 5/11* (2006.01)
(Continued)

(52) U.S. Cl.
CPC .......... *A61B 5/1116* (2013.01); *A61B 5/04888* (2013.01); *A61B 5/11* (2013.01);
(Continued)

(58) Field of Classification Search
CPC .......... A61H 1/00; A61H 1/02; A61H 1/0237; A61H 1/024; A61H 1/0244; A61H 1/0262; A61H 3/00; A61H 2201/16; A61H 2201/1628; A61H 2201/163; A61H 2201/164; A61H 2201/1642; A61H 2201/50; A61H 2201/5005; A61H 2201/5007; A61H 2201/5058; A61H 2201/5061; A61H 2201/5064; A61H 2201/5069; A61H 2201/5071; A61H 2201/5079; A61H 2201/5084; A61H 2203/00; A61H 2203/04; A61H 2203/0406; A61H 2205/00; A61H 2205/10; A61H 2205/102
See application file for complete search history.

(56) References Cited

U.S. PATENT DOCUMENTS 9,314,394 B2 *  4/2016  Hirata ............... A61H 3/00
2005/0177080 A1*  8/2005  Yasuhara ............ A61B 5/112
602/16
(Continued)

FOREIGN PATENT DOCUMENTS

CN   201642750 U    11/2010
EP   2 138 146 A1   12/2009
(Continued)

OTHER PUBLICATIONS

Supplementary European Search Report dated Jun. 18, 2015.
(Continued)

*Primary Examiner* — Steven Douglas
(74) *Attorney, Agent, or Firm* — Collard & Roe, P.C.

(57) ABSTRACT

In a wearable motion assist device, a motion assist device for generating a motion pattern synchronized with a wearer while maintaining a certain phase difference between a motion of the wearer and a motion of the device, and a synchronization based control method for the device are
(Continued)

provided. The motion assist device acquires a phase of torque generated by the wearer's motion, applies a value of the phase to a phase oscillator model as an input, performs arithmetic processing, and calculates target torque and a target angle of the device with the motion of the device synchronized with the wearer. It is possible to improve an assisting effect of the device by controlling the device based on the calculated values.

10 Claims, 11 Drawing Sheets

(51) Int. Cl.
    *A61H 3/00*         (2006.01)
    *A61B 5/0488*     (2006.01)
    *A61B 5/22*         (2006.01)
    *A61B 5/00*         (2006.01)
    *A61H 1/02*         (2006.01)
    *B25J 9/16*          (2006.01)
    *G09B 19/00*      (2006.01)

(52) U.S. Cl.
    CPC ............ *A61B 5/1121* (2013.01); *A61B 5/224* (2013.01); *A61B 5/6811* (2013.01); *A61H 1/024* (2013.01); *A61H 3/00* (2013.01); *B25J 9/1615* (2013.01); *G09B 19/003* (2013.01); *A61H 2201/1215* (2013.01); *A61H 2201/165* (2013.01); *A61H 2201/5007* (2013.01); *A61H 2201/5061* (2013.01); *A61H 2201/5069* (2013.01); *A61H 2201/5092* (2013.01); *G05B 2219/45109* (2013.01)

(56) References Cited

U.S. PATENT DOCUMENTS

| | | | |
|---|---|---|---|
| 2009/0062884 A1* | 3/2009 | Endo | A61N 1/0452 607/49 |
| 2009/0137366 A1* | 5/2009 | Hirata | A61B 5/02438 482/9 |
| 2010/0049102 A1 | 2/2010 | Yasuhara | |
| 2010/0130893 A1 | 5/2010 | Sankai | |
| 2010/0132464 A1 | 6/2010 | Yasuhara | |
| 2010/0271051 A1 | 10/2010 | Sankai et al. | |
| 2011/0264015 A1 | 10/2011 | Endo | |
| 2011/0288453 A1 | 11/2011 | Endo | |
| 2014/0221894 A1* | 8/2014 | Nagasaka | A61H 3/00 602/23 |

FOREIGN PATENT DOCUMENTS

| | | |
|---|---|---|
| JP | 2005-305615 A | 11/2005 |
| JP | 3930399 B2 | 6/2007 |
| JP | 4744585 B2 | 8/2011 |
| JP | 2012-066375 A | 4/2012 |
| WO | 2009/084387 A1 | 7/2009 |

OTHER PUBLICATIONS

International Search Report of PCT/JP2012/083326, mailed Feb. 12, 2013.
Zhang Xia et al., "Shinkei Shindoshi o Mochiita Hoko Assist Sochi no Docho Seigyo", The 12th Symposium on Construction Robotics in Japan Ronbunshu, Sep. 7, 2010, pp. 181-188.
Yasuhiro Wakui et al., "Sychronization Based Control of a Motion Assist System Using Vector Field", The Japan Society of Mechanical Engineers Hokuriku Shin'etsu Branch Dai 48 Ki Sokai Koenkai Koen Ronbunshu, Mar. 1, 2011, pp. 151-152.
Gen Aoyama et al., "Walking Pattern Generation based on the Interaction of Phase Oscillators and Dynamical Models", IEICE Technical Report, Mar. 11, 2002, pp. 175-182, vol. 101, No. 735.
Minoru Hashimoto et al., "Synchronization Based Control of Robotic Suits Using a Phase Oscillator", The 13th Symposium on Construction Robotics in Japan Ronbunshu, Sep. 11, 2012, pp. 213-220.
Zhang Xia, "Synchronization Control for Motion Assist Using Neural Oscillators", Feb. 11, 2009, pp. 1-71, with English Abstract.
Shin'Ya Kotosaka et al., "Robot Drumming by Neural Oscillator", 1999, vol. 3, pp. 1221-1222.
Koji Ito, "Embodied Intelligence System Theory", Kyoritsu Shuppan Co., LTD, 2005, pp. 154-166 with index.
Satohsi Ito et al., "A Model of Adaptation to Environmental Changes in Rhythmic Movements", 1998, pp. 1237-1245, vol. 34, No. 9.

* cited by examiner (a)K=0.1

(c)K=5.0

MOVEMENT ASSISTANCE DEVICE, AND SYNCHRONY BASED CONTROL METHOD FOR MOVEMENT ASSISTANCE DEVICE

CROSS REFERENCE TO RELATED APPLICATIONS

This application is the National Stage of PCT/JP2012/083326 filed on Dec. 21, 2012, which claims priority under 35 U.S.C. §119 of Japanese Application No. 2011-279362 filed on Dec. 21, 2011, the disclosures of which are incorporated by reference. The international application under PCT article 21(2) was not published in English.

TECHNICAL FIELD

The present invention relates to a wearable motion assist device and a synchronization based control method for the wearable motion assist device.

In recent years, a shortage of care workers who support elderly people has been a problem. Accordingly, research and development of welfare robots has been conducted briskly (Patent Document 1). It is expected that a wearable motion assist device, which is a kind of welfare robots, will be put to practical use as support for elderly people's daily life.

As one of control methods for such a wearable motion assist tool, a control method called synchronization based control for achieving a coordinated movement of a human and a device has been proposed (Non Patent Document 1). Synchronization based control makes it possible to adjust synchronism between a human and a device. By increasing synchronism, a device can be used for assistance to movement in which the device synchronizes its motion timing with that of a human. Conversely, it is expected that a device will be used as movement teaching rehabilitation in which the device hauls a human by reducing synchronism. A wearable movement support device for assisting a wearer to move more comfortably by this synchronization based control has been proposed until now (Patent Document 2).

PRIOR ART DOCUMENT

Patent Document

[Patent Document 1] International Publication No. WO 2009/084387 A
[Patent Document 2] JP Patent Application Publication No. 2012-66375 A
[Patent Document 3] JP Patent Application Publication No. 2005-305615 A

Non Patent Document

[Non Patent Document 1] Zhang Xia, "Synchronization Control for Motion Assist Using Neural Oscillators", 2007, Master Thesis, Graduate School of Science and Technology, Shinshu University
[Non Patent Document 2] Shin'ya Kotosaka, Strefan Schaal, "Parameter Learning of Neural Oscillators for Generating Blow Movement of a Robot", Proceedings of the 17th Annual Conference of the Robotics Society of Japan, 1999, Vol. 3, p. 3541-3547
[Non Patent Document 3] Gen Aoyama, Toshiyuki Kondo, Satoshi Murata, Koji Ito, "Walking Pattern Generation Based on the Interaction of Phase Oscillators and Dynamical Models", The Institute of Electronics, Information and Communication Engineers, 2002, NC2001-155
[Non Patent Document 4] Koji Ito, "Shintaichi Shisutemuron (Embodied Intelligence System Theory)", Kyoritsu Shuppan Co., Ltd., 2005
[Non Patent Document 5] Satoshi Ito, Hideo Yuasa, Zhi-wei Luo, Masami Ito, Dai Yanagihara, "A Model of Adaptation to Environmental Changes in Rhythmic Movements", The Society of Instrument and Control Engineers collected papers, Vol. 34, No. 9, p. 1237-1245

SUMMARY OF THE INVENTION

Problems to be Solved by the Invention

A mutually inhibiting model of a neural oscillator is used for generating a movement pattern of synchronization based control in a wearable movement support device disclosed in Patent Document 1 (Non Patent Document 2). However, when an articulated object such as a human leg is actuated, a certain phase difference is generated between respective oscillators usually. Accordingly, there is a problem that, even if the pattern generated by the mutually inhibiting model can perform the synchronization, it is difficult to generate a phase difference. In addition, there is a problem that, when a motion pattern is generated using the mutually inhibiting model, it is necessary to set almost ten parameters to obtain an arbitrary output waveform for an oscillation input, and that adjustment thereof is difficult.

The present invention was made in view of solving the above described problems, and its object is to provide a motion assist device that allows motion with an arbitrary phase difference being generated in motions between a human and a motion assist device. In addition, another object of the present invention is to provide a control method for the motion assist device for controlling the motion assist device simply with a small number of parameters.

Means for Solving Problems

Namely, a motion assist device to solve the above described problems includes: a joint disposed corresponding to a wearer's bent movable region; a link connected to the joint, the link being installed in the wearer; an actuator configured to drive a motion of the joint; a phase acquisition unit configured to acquire a phase $\theta'_h$ of a motion of the wearer's bent movable region; a target value calculation unit configured to calculate a target value of motion of the joint for synchronizing the motion of the wearer's bent movable region and the motion of the joint while maintaining a preset target phase difference based on a phase oscillator model whose the phase $\theta'_h$ of the motion of the bent movable region acquired by the phase acquisition unit is an input oscillation; and a drive control unit configured to drive the actuator based on the target value of motion calculated by the target value calculation unit.

In the motion assist device, the phase acquisition unit includes an interaction force detection sensor configured to detect interaction force of the motion of the wearer's bent movable region and the motion of the joint; a joint angle sensor configured to detect a joint angle of the joint; and a phase estimation unit configured to estimate the phase $\theta'_h$ of the motion of the wearer's bent movable region based on the interaction force detected by the interaction force detection sensor and the joint angle detected by the joint angle sensor.

In the motion assist device, the phase estimation Unit estimates torque $\tau'_h$ of the wearers bent movable region by the following Equation (1) from interaction force $\lambda$ detected by the interaction force detection sensor and the joint angle q detected by the joint angle sensor;

$$\tau'_h = M_h \ddot{q} + G_h q + \lambda \quad (1)$$

(in Equation (1), $M_h$ and $G_h$ denote a human inertia term and a gravity Lenin, respectively)

estimates maximum torque $\tau'_{h\_max}$ and minimum torque $\tau'_{h\_min}$ of a human in motion by further using the Equation (I), substitutes $\tau'_{h\_max}$ and $\tau'_{h\_min}$ into the following Equation (2), and calculates amplitude $A'_h$ of the estimated torque $\tau'_h$;

$$A'_h = \frac{\tau'_{h\_max} - \tau'_{h\_min}}{2} \quad (2)$$

calculates a y-coordinate of a phase angle on polar coordinates by the following Equation (3) from the torque $\tau'_h$ and the amplitude $A'_h$;

$$y = \frac{\tau'_h - (A'_h + \tau'_{h\_min})}{A'_h} \quad (3)$$

calculates an x-coordinate by the following Equation (4) from the Pythagorean theorem;

•$\dot{y} \geq 0$ •$\dot{y} < 0$ $$x = \sqrt{1-y^2} \quad x = \sqrt{1-y^2} \quad (4)$$

performs polar coordinate transformation by the following Equation (5); and $$\theta'_h = \alpha \tan 2(y,x)(-\pi \leq \theta'_h \leq \pi) \quad (5)$$

estimates the phase $\theta'_h$ of the motion of the wearer's bent movable region.

In the motion assist device, the target value calculation unit calculates driving torque of the joint by Output of Equation (7) as the target value of motion based on a mathematical model composed of a phase oscillator that has relationships of the following Equation (6) and Equation (7)

$$\dot{\theta}_\alpha = \omega_\alpha + K \sin(\theta'_h - \theta_\alpha + \theta_d) \quad (6)$$

$$\text{Output} = A_\alpha \sin \theta_\alpha - A_\alpha \sin \theta_{\alpha\theta} \quad (7)$$

(in Equation (6), $\omega_\alpha$, $\theta_\alpha$, and K denote a natural frequency, phase angle, and synchronization gain of the joint, respectively, and $\theta_d$ denotes the target phase difference, and in Equation (7), $A_\alpha$ and $\theta_{\alpha\theta}$ denote amplitude of an Output waveform and an initial phase of an oscillator, respectively, and a second term of a right side in Equation (7) is a term for setting an initial value of the Output waveform at 0).

In the motion assist device, the drive control unit performs feedback control of the actuator based on the target value of motion calculated by the target value calculation unit.

A synchronization based control method for a motion assist device includes a joint disposed corresponding to a wearer's bent movable region, a link connected to the joint, the link being installed in the wearer, an actuator configured to drive a motion of the joint, and assisting a motion of the wearer, the control method comprising: a phase acquisition step of acquiring a phase $\theta'_h$ of a motion of the wearer's bent movable region; a target value calculation step of calculating a target value of motion of the joint for synchronizing the motion of the wearer's bent movable region and the motion of the joint while maintaining a preset target phase difference based on a phase oscillator model with the phase $\theta'_h$ of the motion of the bent movable region acquired in the phase acquisition step being an input oscillation; and a drive control step of driving the actuator based on the target value of motion calculated in the target value calculation step.

In the synchronization based control method for the motion assist device, the phase acquisition step includes an interaction force detection step of detecting interaction force of the motion of the wearer's bent movable region and the motion of the joint; a joint angle detection step of detecting a joint angle of the joint; and a phase estimation step of estimating the phase $\theta'_h$ of the motion of the wearer's bent movable region based on the interaction force detected in the interaction force detection step and the joint angle detected in the joint angle detection step.

In the synchronization based control method for the motion assist device, the phase estimation step includes: a torque estimation step of estimating torque $\tau'_h$ of the wearer's bent movable region by Equation (1) from interaction force $\lambda$ detected in the interaction force detection step and the joint angle q detected in the joint angle detection step; a torque amplitude calculation step of estimating maximum torque $\tau'_{h\_max}$ and minimum torque $\tau'_{h\_min}$ of a human in motion by further using above Equation (1); substituting $\tau'_{h\_max}$ and $\tau'_{h\_min}$ into Equation and calculating amplitude $A'_h$ of the estimated torque $\tau'_h$; a y-coordinate calculation step of calculating a y-coordinate of a phase angle on polar coordinates by Equation (3) from the torque $T'_h$ and the amplitude $A'_h$; an x-coordinate calculation step of calculating an x-coordinate by Equation (4) from the Pythagorean theorem; and a phase transformation step of performing polar coordinate transformation by Equation (5), and calculating a phase $\theta'h$ of the motion of the wearer's bent movable region.

As regards synchronization based control method for the motion assist device, in the target value calculation step, driving torque of the joint is calculated by Output of Equation (7) as the target value of motion based on a mathematical model composed of a phase oscillator that has relationships of Equation (6) and Equation (7).

As regards synchronization based control method for the motion assist device, in the drive control step, feedback control of the actuator is performed based on the target value of motion calculated by the target value calculation unit.

Effects of the Invention

The motion assist device and the synchronization based control method therefor according to the present invention employ a phase oscillator model as an oscillator model used at a time of generating a movement pattern that determines an output of the motion assist device, make the wearer's motion an input oscillation of the phase oscillator, and make it possible to generate a pattern with an arbitrary phase difference generated with respect to a motion of a human. This makes it possible to perform synchronization based control so that the motion assist device moves in synchronization while maintaining the arbitrary phase difference from the wearer's motion.

The wearable motion assist device and the synchronization based control method therefor according to the present invention make it possible to perform motion pattern generation for the motion assist device efficiently by simple parameter setting.

MODE FOR CARRYING OUT THE INVENTION

The following describes a wearable motion assist device and an embodiment for performing a synchronization based control method therefor according to the present invention.

<Phase Oscillator Model>

First, a phase oscillator model will be described. The phase oscillator model is a pattern generation model used between oscillators that perform simple harmonic oscillation. The phase oscillator model, which allows synchronization with another oscillator and preparation of a phase difference, is used for movement pattern generation or the like for each joint of an articulated robot (Patent Document 3, Non Patent Documents 3 to 5). In these pieces of existing research, pattern generation according to the phase oscillator model is performed in order to control a motion of each joint of the articulated robot and a motion of right and left legs of a bipedal walking robot. On the other hand, the present invention is a control method for performing motion pattern generation according to the phase oscillator model by using a wearer's motion as an input oscillation in a motion of the motion assist device that is installed in a human body, and is novel in that processing is not performed in an identical robot. In addition, the present invention is novel in that, on an assumption that part of the wearer's body is also one oscillator, a motion between the human body and the device is controlled based on synchronization while maintaining an arbitrary phase difference.

Figure 1:
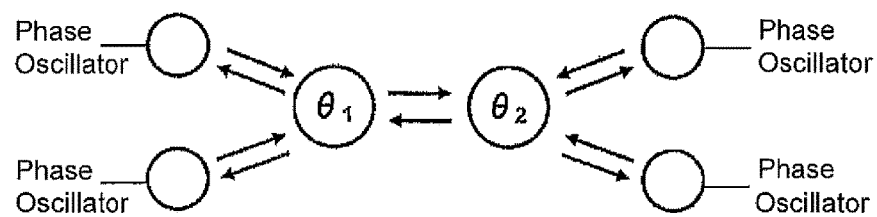
FIG. 1 is a diagram of a model illustrating connection of a plurality of phase oscillators.

FIG. 1 illustrates a model illustrating connection of a plurality of phase oscillators, and the following Equation (8) expresses a model equation of the phase oscillators.

$$\dot{\theta}_i = \omega_i + \sum_{j=1}^{n} K_{ij} \sin(\theta_j - \theta_i) \quad (8)$$

In Equation (8), $\theta$ denotes a phase angle of each of the oscillators, $\omega$ denotes a natural angular frequency, n denotes a number of adjacent oscillators, and $K_{ij}$ denotes strength of an interaction that takes place between oscillators i-j. A second term of a right side is an interaction term between the oscillators, which causes entrainment and synchronization among the plurality of oscillators. Equation (8) is an equation representing that an oscillator i interacts with n oscillators. j (=1 to n) represents a surrounding oscillator.

<Overview of Synchronization Based Control>

Figure 2:
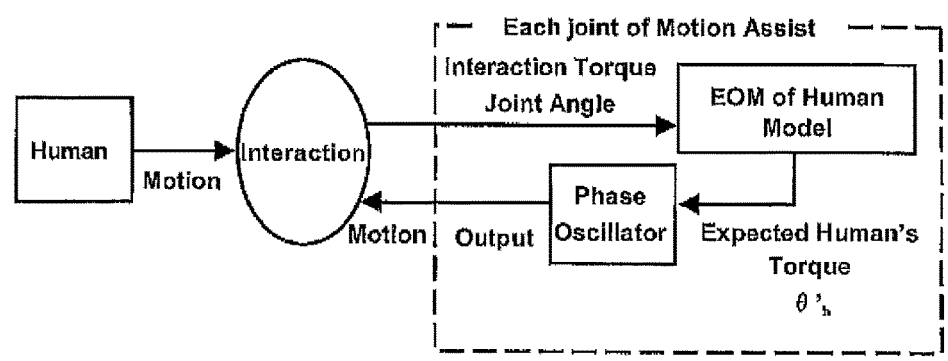
FIG. 2 is a schematic diagram of synchronization based control in the present invention.

FIG. 2 illustrates an example of an overview of synchronization based control according to the present invention. First, a wearer's torque (Expected Human's Torque) is estimated from interaction force (Interaction Torque) which arises from an interaction of a motion of a joint (Each joint of Motion Assist) of a device and a motion of the wearer's (Human) bent movable region, and from a joint angle of the device. Next, a phase $\theta'_h$ of the torque is estimated as a phase $\theta'_h$ of the wearer's motion from the wearer's estimated torque (EOM (Estimation Of Motion) of Human Model). Next, the phase $\theta'_h$ of the wearer's motion is substituted into the model equation of a phase oscillator as an input oscillation of the phase oscillator, and arithmetic is performed. Target values (Output) of motion, such as target torque and a target angle, are calculated by the model equation of the phase oscillator as an output that synchronizes with the wearer's motion. At this time, in the model equation for performing arithmetic processing, it is possible to generate an arbitrary phase difference for an input. Then, next motion of the device is generated according to the target value of motion. By repeating such a series of motions, a motion of the device is synchronized with the wearer's motion.

<Example of a Model of the Wearer's Bent Movable Region>

Figure 3:
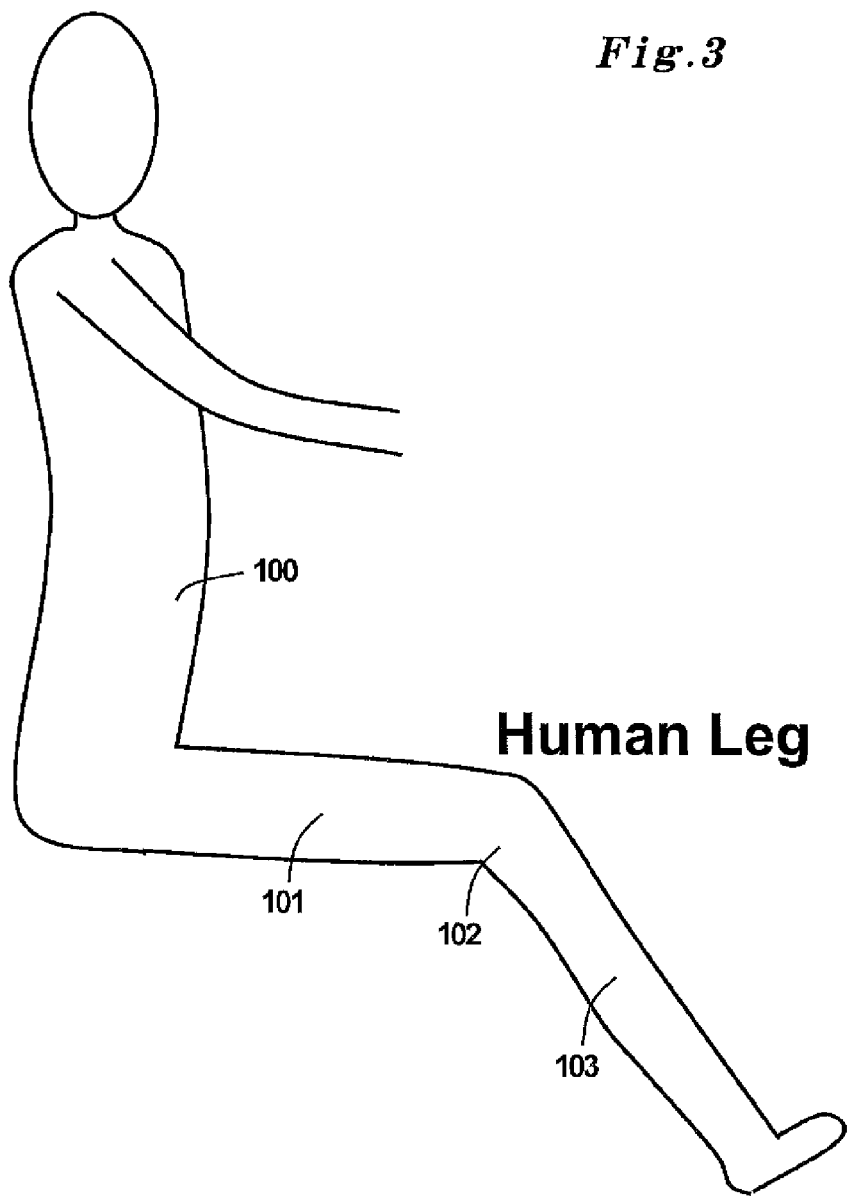
FIG. 3 is a diagram illustrating a human body that serves as a wearer.
Figure 4:
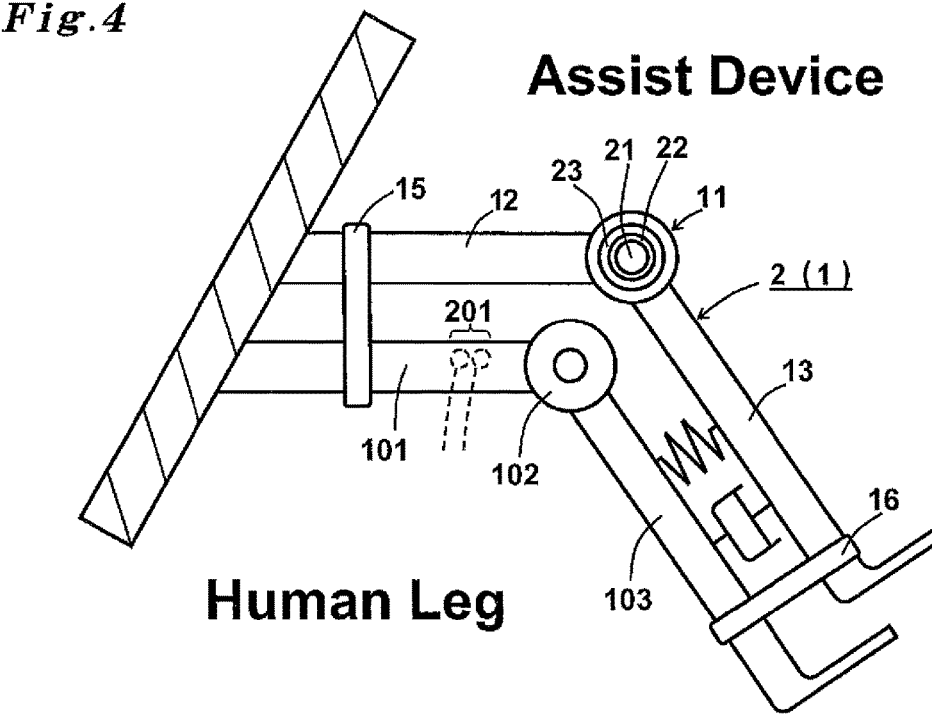
FIG. 4 is a diagram representing a leg of the human body illustrated in FIG. 3 with a single-degree-of-freedom knee-joint model, and illustrating a usage condition in a state in which a movable mechanism of a motion assist device of the present invention is installed in the single-degree-of-freedom knee joint model.

FIG. 3 illustrates a human body 100 that serves as a wearer. Herein, as an example, an example in which the wearer's bent movable region (joint) is a knee joint is illustrated. The human body 100 has a thigh region 101, a knee joint 102, and a leg region 103 as a leg (Human Leg). FIG. 4 illustrates a single-degree-of-freedom knee joint model (Human Leg) that models the leg of the human body illustrated in FIG. 3. FIG. 4 illustrates a movable mechanism 2 of the motion assist device 1 in a state of installation in the single-degree-of-freedom knee joint model. The motion assist device estimates a phase of a torque waveform of the knee joint 102 (an example of the bent movable region) as a phase of the motion of the bent movable region based on an estimated value of the wearer's torque in the present model.

<Example of a Configuration of the Motion Assist Device>

The movable mechanism 2 of the motion assist device 1 illustrated in FIG. 4 includes a joint 11, a link 12, a link 13, an actuator 21, an interaction force detection sensor 22, a joint angle sensor 23, an installation tool 15, and an installation tool 16. A resistor and a piston pump illustrated in FIG. 4 equivalently represent that the device 1 gives load and driving force to the human leg, and do not constitute the device 1.

The joint 11 is disposed corresponding to the knee joint 102 that is the wearer's bent movable region. In this example, the joint 11 for rotating with single degree of freedom (one axis) is used corresponding to a degree of freedom of the knee joint 102. Herein, when a motion assist device is installed in a bent movable region that moves with multiple degrees of freedom such as a wrist, it is preferable to use a joint that has multiple degrees of freedom.

The joint 11 connects the link 12 and the link 13. This makes the link 12 and the link 13 rotatable around the joint 11 as a pivot. The link 12 is formed to have a length installable along the thigh region 101, and has the installation tool 15 for fixing the link 12 to the thigh region 101. The installation tool 15 is, for example, a belt for fastening and fixing the link 12 and the thigh region 101 together. The link 13 is formed to have a length installable along the leg region 103, and has the installation tool 16 for fixing the link 13 to the leg region 103. The installation tool 16 is, for example, a belt for fastening and fixing the link 13 and the leg region 103 together. Herein, for example, as in a case of installation of the motion assist device 1 in a wearer in a state of sitting on a chair, even if the installation tool 15 is not provided, when it is possible to fix a position of the link 12 relative to the wearer, the link 12 may not have the installation tool 15. That is, only a link that moves together with a motion of the wearer's bent movable region needs to have the installation tool.

The actuator 21 drives a motion of the joint 11. The actuator 21 is, for example, an electric-powered motor. Hereinafter, the actuator 21 is also referred to as a motor 21. A motion of the actuator 21, such as a rotational speed, rotational angle, and rest position, is controlled by a drive control unit 34 to be described later. Driven by the actuator 21, the joint 11 moves, and the link 12 and the link 13 move relatively. A speed reducer with an appropriate reduction ratio may be attached to the motor 21.

The interaction force detection sensor 22 detects interaction force generated by a motion of the wearer's knee joint 102 and a motion of the joint 11, and is provided in the joint 11. As the interaction force detection sensor 22, a torque sensor is used in this example. Hereinafter, the interaction force detection sensor 22 is also referred to as a torque sensor 22. As the interaction force detection sensor 22, a force sensor or a wrist force sensor that detects force may be used to calculate torque.

The joint angle sensor 23 detects a joint angle of the joint 11. Since the joint angle can be determined from the rotational angle of the motor 21, the joint angle sensor 23 may detect the rotational angle of the motor 21. In the present embodiment, an encoder that detects the rotational angle of the motor 21 is used as the joint angle sensor 23. Hereinafter, the joint angle sensor 23 is also referred to as an encoder 23.

Figure 5:
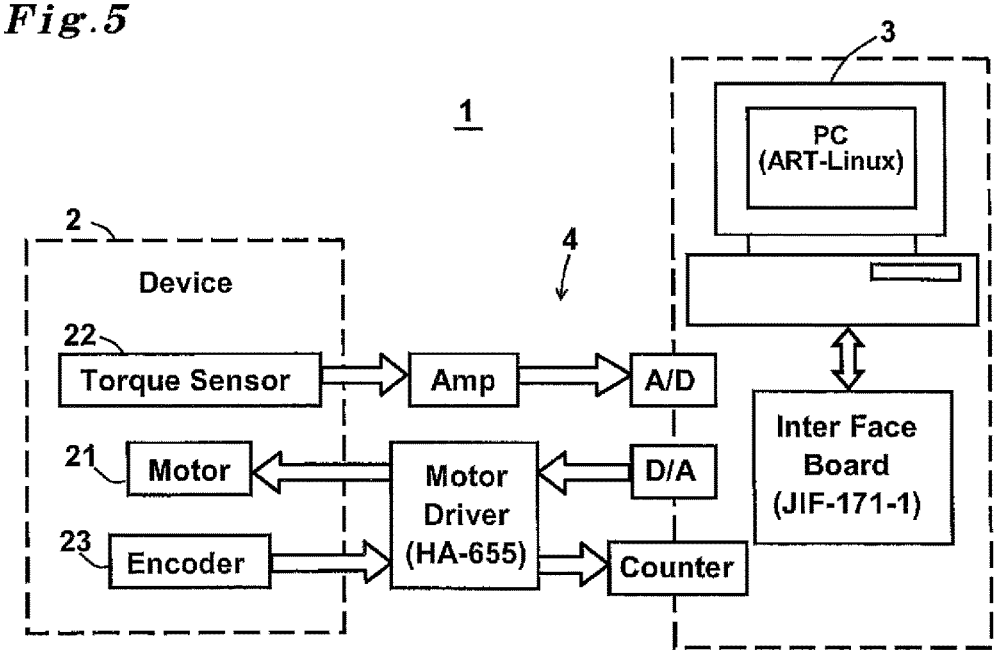
FIG. 5 is a block diagram of an electric system of the motion assist device of the present invention.

FIG. 5 illustrates a block diagram of an electric system of the motion assist device 1.

The motion assist device 1 includes a movable mechanism 2, a computer (PC) 3, and an interface circuit 4. As described above, the movable mechanism 2 includes the motor 21, the torque sensor 22, and the encoder 23. The computer 3 is intended to control a motion of the movable mechanism 2. The computer 3 operates in accordance with a program stored in a built-in memory. As the computer 3, a general-purpose computer including a body and a display as illustrated in FIG. 5 may be used, or the computer 3 may be downsized using a substrate, a module, and the like on which a central processing unit (CPU), a memory for storing the program, and the like are mounted.

The interface circuit 4 is a circuit for connecting the movable mechanism 2 and the computer 3. The interface circuit 4 includes, for example, an amplifier (Amp) for amplifying a detection value of the torque sensor 22 to an appropriate level, an analog-to-digital converter (A/D) for converting an output of the amplifier from an analog signal into a digital signal, a motor driver, a digital-to-analog converter (D/A) for converting a digital signal for driving the motor 21 outputted from the computer 3 into an analog signal, and a counter for inputting an output of the encoder 23 into the computer 3. Herein, a general-purpose inter face board installed in an expansion card slot of the computer 3 is used, the inter face board including A/D, D/A, and the counter.

The computer 3 and the interface circuit 4 may be downsized and integrated with the movable mechanism 2. In this case, preferably the device 1 has a built-in battery and operates on the battery.

Figure 6:
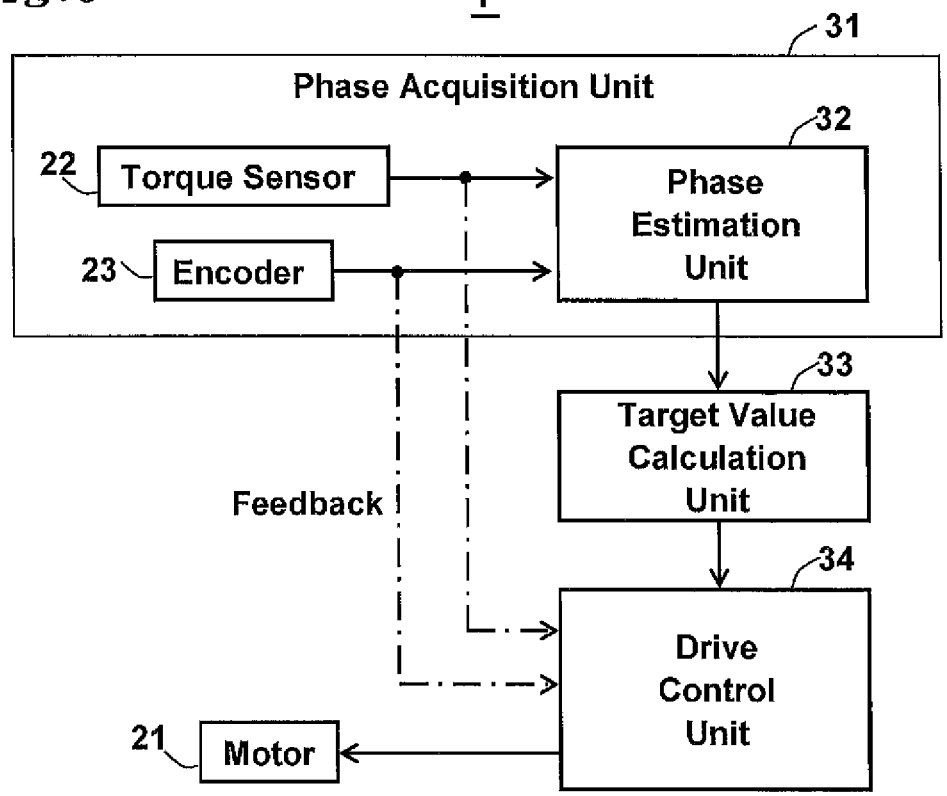
FIG. 6 is a block diagram illustrating functions of the motion assist device of the present invention.

By operating in accordance with the program, the computer 3 functions as a phase estimation unit 32, a target value calculation unit 33, and a drive control unit 34, as illustrated in FIG. 6. As illustrated in FIG. 6, a phase acquisition unit 31 includes the torque sensor (interaction force detection sensor) 22, the encoder (joint angle sensor) 23, and the phase estimation unit 32. The phase acquisition unit 31 acquires a phase $\theta'_h$ of a motion of the wearer's bent movable region. The phase estimation unit 32 estimates the phase $\theta'_h$ of the motion of the wearer's bent movable region based on the interaction force (torque) detected by the torque sensor 22 and the joint angle detected by the encoder 23. The target value calculation unit 33 calculates a target value of motion of the joint 11 for synchronizing a motion of the wearer's bent movable region (knee joint 102) and a motion of the joint 11 based on a phase oscillator model with the phase $\theta'_h$ of the motion of the bent movable region being an input oscillation while maintaining a preset target phase difference. The target value of motion is, for example, target torque and target joint angle of the joint 11. The drive control unit 34 drives the motor 21 based on the target value of motion calculated by the target value calculation unit 33.

<Application of the Phase Oscillator Model to the Synchronization Based Control>

The model equation of a phase oscillator is a pattern generation model used among the oscillators that perform a simple harmonic oscillation. In order to achieve synchronization of motions between the phase oscillator that generates a motion of the motion assist device 1 and the wearer, it is assumed that the wearer also moves in accordance with an oscillator similar to the oscillator of the device, and a phase of the motion of the wearer's bent movable region is estimated. The following describes details.

Figure 7:
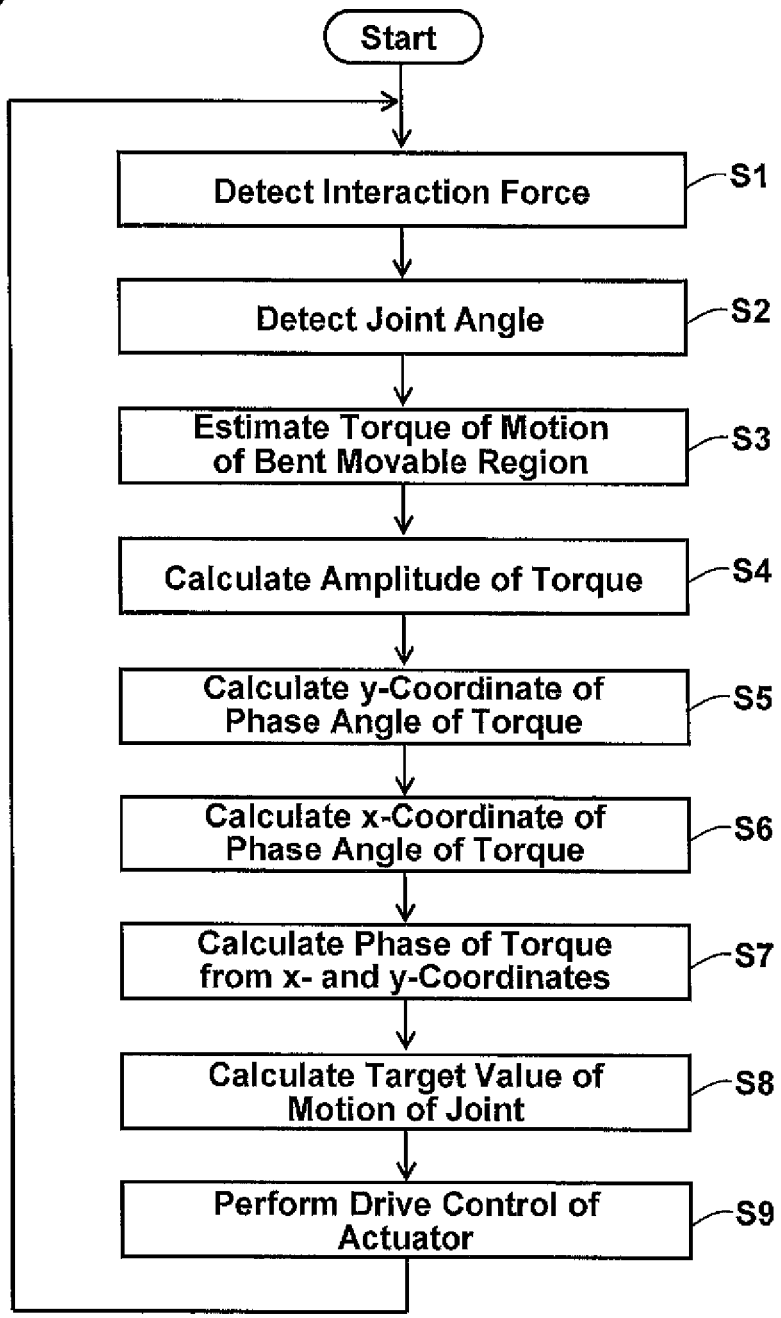
FIG. 7 is a flow chart illustrating a synchronization based control method of the motion assist device of the present invention.

FIG. 7 is a flow chart illustrating a synchronization based control method for the motion assist device 1.

In an interaction force detection step S1, the computer 3 (see FIG. 5) detects interaction force of the motion of the wearer's bent movable region and the motion of the joint 11 from the torque sensor 22. Then, in a joint angle detection step S2, the computer 3 detects the joint angle of the joint 11 from the encoder 23. Although either step S1 or step S2 may be performed first, step S1 and step S2 are performed almost simultaneously.

Subsequently, in a torque estimation step S3, the computer 3 estimates $\tau'_h$ torque of a motion of the wearer's bent movable region (knee joint 102). The torque $\tau'_h$ is calculated by an estimation equation expressed by the following Equation (1).

$$\tau'_h = M_h \ddot{q} + G_h q + \lambda \qquad (1)$$

In Equation (1), $M_h$, $G_h$, and $\lambda$ denote a human inertia term, a gravity term, and interaction force, respectively. The interaction force is a detection value of the torque sensor 22. The human inertia term and the gravity term may be determined from an existing known database, or measured values may be used. Examples of known databases include a document "Michiyoshi Ae, Tang Hai-peng, Takashi Yokoi, "Estimation of Inertia Properties of the Body Segments in Japanese Athletes", the Biomechanism 11, (1992), pp. 23-33". On an assumption that a joint angle q of the bent movable region (knee joint) when the device is installed and a joint angle of the joint 11 are equivalent, a joint angle determined from a detection value of the encoder 23 is defined as q.

Furthermore, in a torque amplitude calculation step S4, the computer 3 determines maximum torque $\tau'_{h\_max}$ and minimum torque $\tau'_{h\_min}$ of the human in motion by using Equation (1). Amplitude $A'_h$ of the estimated torque is determined by substituting maximum torque $\tau'_{h\_max}$ and minimum torque $\tau'_{h\_min}$ into the following Equation (2).

$$A'_h = \frac{\tau'_{h\_max} - \tau'_{h\_min}}{2} \quad (2)$$

In Equation (2), as the maximum torque $\tau'_{h\_max}$ and minimum torque $\tau'_{h\_min}$, values of a motion one period before the time of arithmetic are used. An initial value is set at an arbitrary value.

Subsequently, in a y-coordinate calculation step S5, the computer 3 calculates a y-coordinate of the phase angle on polar coordinates by the following Equation (3) from $\tau'_h$ determined by Equation (1) and $A'_h$ determined by Equation (2).

$$y = \frac{\tau'_h - (A'_h + \tau'_{h\_min})}{A'_h} \quad (3)$$

Next, in an x-coordinate calculation step S6, the computer 3 calculates an x-coordinate by the following Equation (4) from the Pythagorean theorem.

$$\dot{y} \geq 0 \quad \dot{y} < 0$$
$$x = \sqrt{1-y^2} \quad x = -\sqrt{1-y^2} \quad (4)$$

Next, in a phase transformation step S7, the computer 3 performs, by the following Equation (5), polar coordinate transformation of the y-coordinate and x-coordinate calculated by Equation (3) and Equation (4), respectively, to determine the phase (phase angle) $\theta'_h$ of the motion (torque) of the wearer's bent movable region.

$$\theta'_h = \alpha \tan 2(y,x)(-\pi \leq \theta'_h \leq \pi) \quad (5)$$

Thus, it is possible to estimate (acquire) the phase $\theta'_h$ of the motion of the wearer's bent movable region.

Next, in a target value calculation step S8, the computer 3 calculates a target value of motion of the joint 11 for synchronizing the motion of the wearer's bent movable region and the motion of the joint 11 while maintaining the preset target phase difference based on the phase oscillator model with the phase $\theta'_h$ of the motion of the bent movable region acquired in the phase estimation step (steps S1 to S7) being an input oscillation.

The target value of motion is calculated based on a mathematical model composed of a phase oscillator having relationships of Equation (6) and Equation (7) described below.

First, a phase angle of the joint 11 is calculated by the following Equation (6) that is based on the phase oscillator model of Equation (8). The phase $\theta'_h$ is inputted into the following Equation (6).

$$\dot{\theta}_a = \omega_a + K \sin(\theta'_h - \theta_a + \theta_d) \quad (6)$$

In Equation (6), $\omega_a$, $\theta_a$, and K are a natural frequency, phase angle, and synchronization gain of the device 1, respectively, and $\theta_d$ denotes a target phase difference between the motion of the wearer's bent movable region and the motion of the joint 11 of the device 1.

The computer 3 makes Output determined by the following Equation (7) from the phase angle of the joint 11 of the device 1 determined by Equation (6) as a target value of motion. In this example, an output waveform of Output is defined as driving torque to be generated by the joint 11.

$$Output = A_a \sin \theta_a - A_a \sin \theta_{a0} \quad (7)$$

In Equation (7), $A_a$ and $\theta_{a0}$ denote amplitude of the output waveform and an initial phase of the oscillator, respectively. In addition, a second term in a right side in Equation (7) is a term for setting an initial value of the output at 0.

Next, in a drive control step S9, the computer 3 performs drive control of the actuator 21 based on the target value of motion. Specifically, the computer 3 generates a motion pattern for the motor 21 and drives the motor 21 so that the joint 11 generates the driving torque with the waveform of Output that is the target value of motion.

In the drive control step S9, the motor 21 is preferably feedback-controlled based on the target value of motion.

The computer 3 repeats a series of motions of steps S1 to S9.

Herein, the computer 3 (see FIG. 5) operates as the phase estimation unit 32 (see FIG. 6) in the interaction force detection step S1, the joint angle detection step S2, the torque estimation step S3, the torque amplitude calculation step S4, the y-coordinate calculation step S5, the x-coordinate calculation step S6, and the phase transformation step S7. The computer 3 operates as the target value calculation unit 33 (see FIG. 6) in the target value calculation step S8, and operates as the drive control unit 34 in the drive control step S9. In addition, the interaction force detection step S1 to the phase transformation step S7 correspond to a phase acquisition step of acquiring the phase $\theta'_h$ of the motion of the wearer's bent movable region in the present invention. In addition, the torque estimation step S3 to the phase transformation step S7 correspond to a phase estimation step of estimating the phase $\theta'_h$ of the motion of the wearer's bent movable region based on the interaction force detected in the interaction force detection step S1 and the joint angle detected in the joint angle detection step S2 in the present invention.

Herein, an example has been described in the target value calculation step S8 in which the waveform of the driving torque of the joint 11 is calculated as a target value of motion. However, the joint angle (target angle) of the joint 11 or the rotational speed of the joint 11 may be calculated as the target value of motion, Since the driving torque, joint angle, and rotational speed of the joint 11 are mutually transformable, a parameter suitable for control may be calculated.

In the present embodiment, the wearer's torque and the phase of the torque are estimated by arithmetic from the interaction force between the wearer and the device, and the joint angle. However, in order to carry out the present invention, an acquisition method of torque and phase is not restricted, but can be suitably changed to another method.

For example, the wearer's accurate torque and phase may be acquired by attaching a sensor directly to the wearer. In this case, it means that the sensor attached to a measurer is connected to the device. When the sensor is attached directly to the wearer to acquire the wearer's torque, steps S1 to S4 of the flow chart in FIG. 7 can be omitted. When the sensor is attached directly to the measurer to acquire the wearer's phase, steps S1 to S7 can be omitted.

An example has been described in which a motion pattern for the device is generated based on a mathematical model of the phase oscillator expressed by Equation (6) and Equation (7). However, a model based on another mathematical model may be used for the mathematical model of the phase oscillator.

An example has been described in which the motion assist device 1 includes the single-degree-of-freedom joint 11. However, the present invention is applicable to a motion assist device that includes a plurality of joints with each of the joints connected by a link. When the plurality of joints are connected by the link, on an assumption that a plurality of phase oscillators correspond to the number of connections of the joints, an influence of each phase oscillator may be added to calculate a phase of motion of the wearer's joint based on Equation (8). For a multi-degree-of-freedom joint, addition and calculation may be performed similarly.

<Synchronization Based Control Experiment by Simulation>

In order to evaluate an effect of the present invention, a verification experiment was conducted by simulation. In the simulation, an interaction between the motion assist device to be controlled based on synchronization and the wearer was simulated on an assumption that the wearer of the device always maintains his or her own motion. In the synchronization based control experiment by the simulation and a real device to be described later, data on a Japanese young man described in the above-described known document "Estimation of Inertia Properties of the Body Segments in Japanese Athletes" was used as an inertia term and a gravity term. Each numerical value used in the simulation was set at each coefficient of $M_h=1.5\times10^{-1}$ kg·m², $M_a=4.1\times10^{-2}$ kg·m², $C_h=0.1$ m²/s, $C_a=0.1$ m²/s, $G_h=5.7$ N·m, $G_a=1.7$ N·m, $k_1=263.6$ N/rad, and $k_2=26.4$ N/rad², where mass of a human leg $m_h=3.0$ kg, length $l_h=3.9\times10^{-1}$ m, mass of a device $m_a=1.0$ kg, and length $l_a=3.5\times10^{-1}$ m.

<Simulation 1>

The simulation was performed with a model of FIG. 4. In addition, the following Equation (9) represents an equation of motion in the present model. In Equation (9), a first term to fourth term of a right side represent an inertia term, a viscous term, a gravity term, and an interaction force term, respectively. Herein, among these terms, the interaction force term was derived using the following Equation (10). (Both coefficients of viscosity $C_h$ and $C_a$ were 0.1 as described above.)

$$\tau = \begin{bmatrix} \tau_h \\ \tau_a \end{bmatrix} = \begin{bmatrix} M_h \ddot{q}_h + C_h \dot{q}_h + G_h + \lambda \\ M_a \ddot{q}_a + C_a \dot{q}_a + G_a - \lambda \end{bmatrix} \quad (9)$$

$$\lambda = k_1(q_l - q_a) + k_2(\dot{q}_l - \dot{q}_a) \quad (10)$$

In the present simulation, the wearer was assumed to maintain a preset torque waveform and to perform a periodic movement. In the present simulation, a frequency of the torque waveform was set at 0.80 Hz, and amplitude was set at 0.80 Nm. The wearer was assumed to determine torque by proportional-derivative (PD) control from a target orbit and a current angle, and to perform movement. Moreover, in the simulation, on an assumption that the device could estimate the wearer's torque accurately, the wearer's torque value was used as it is for an estimated value. A natural angular frequency $\omega_a$ of the oscillator of the device was set at 5.7 rad/s (frequency of 0.90 Hz). An initial phase $\theta_{a0}$ was set at $1.5\pi$ rad. Amplitude $A_a$ of the torque waveform to output was set at 1.0 Nm. According to a flow of the synchronization based control described above, the device was assumed to obtain an output of the phase oscillator based on the estimated value of the wearer's torque. In the present experiment, the simulation was performed of the interaction for each of cases where a target phase difference $\theta_d$ of the device was set at 0 rad and synchronization gains were set at 0.1, 1.0, and 5.0.

Figure 8:
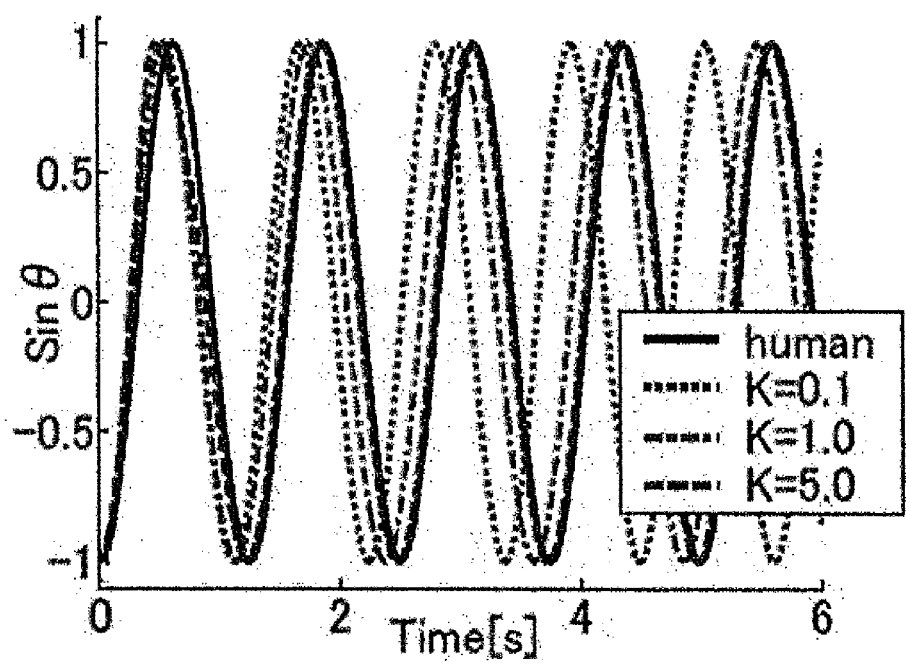
FIG. 8 is a graph of a torque waveform resulting from a synchronization based control simulation.

FIG. 8 illustrates a graph of the torque waveforms resulting from the simulation. Among the waveforms illustrated in FIG. 8, a waveform expressed by a solid line represents a sinusoidal waveform of the wearer's (knee joint 102) phase $\theta'_h$. Waveforms expressed by dashed lines represent sinusoidal waveforms of the phase $\theta_a$ of the device (joint 11) for each of the synchronization gains. It is observed from FIG. 8 that a frequency of the device approaches a natural frequency as the synchronization gain decreases. Conversely, it is observed that the frequency of the device approaches the wearer's frequency as the synchronization gain increases.

Figure 9:
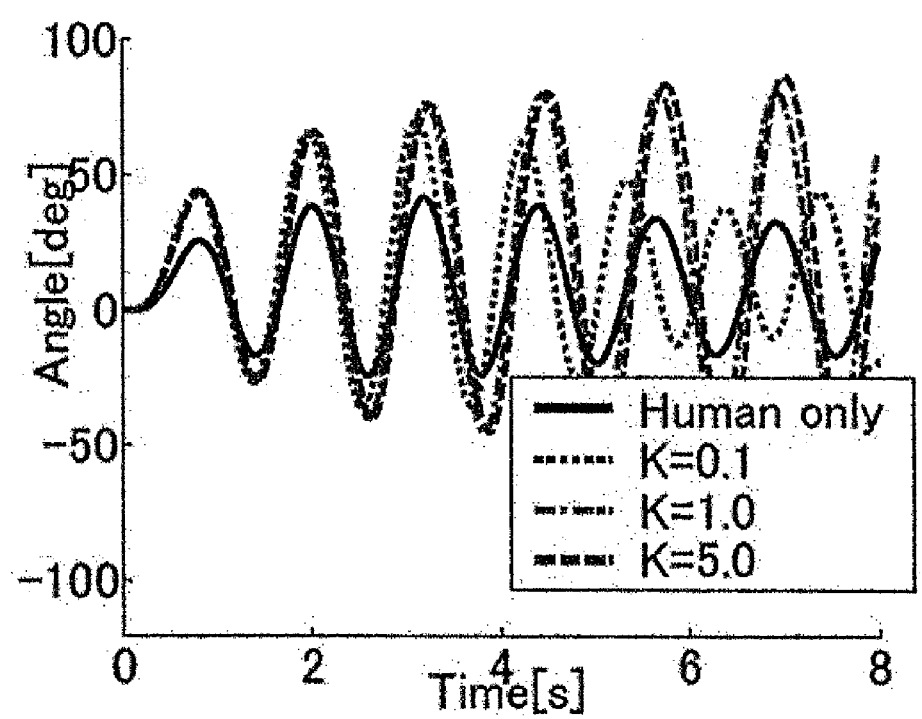
FIG. 9 is a graph of a joint angle resulting from the synchronization based control simulation.

FIG. 9 illustrates a graph of a joint angle of the wearer (knee joint 102) resulting from the simulation. Among waveforms illustrated in FIG. 9, a waveform expressed by a solid line represents a joint angle of the wearer in a case of performing movement without an interaction with the device. Waveforms expressed by dashed lines represent a joint angle of the wearer in a case of interacting with the device controlled with each of the synchronization gains. It is observed from FIG. 9 that the device moves in accordance with the wearer's rhythm, which amplifies amplitude of movement of the knee joint in a case of installing a device with the synchronization gain being set greatly as compared with a case of performing movement without installing the device. This shows that a high assisting effect on the wearer's movement is obtained by controlling the wearable motion assist device 1 by synchronization based control according to the present embodiment.

<Simulation 2>
(Phase Difference Adjustment Experiment by Simulation)

In order to confirm that an output waveform of the motion assist device that moves by the synchronization based control method according to the present invention synchronizes with the wearer's motion while maintaining an arbitrary phase difference, a phase difference adjustment experiment was conducted by simulation. In simulation, the synchronization gain K was set at 5.0. The interaction was simulated for each of cases where target phase differences $\theta_d$ were rad, $0.33\pi$ rad, and $0.67\pi$ rad. Other conditions were similar to conditions of the above-described simulation experiment.

Figure 10:
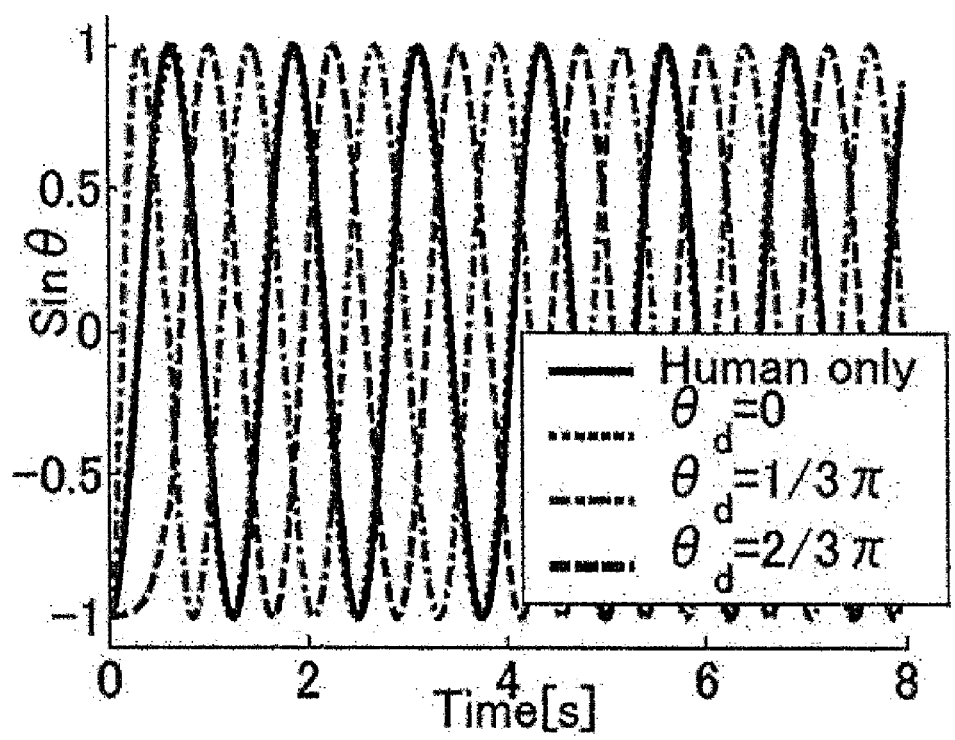
FIG. 10 is a graph of a torque waveform resulting from a phase difference adjustment simulation.

FIG. 10 illustrates a graph of torque waveforms resulting from the simulation. It is observed from FIG. 10 that it is possible to adjust a phase difference of the device from a phase of the wearer's motion by setting a target phase difference.

<Synchronization Based Control Experiment with a Real Device>

As illustrated in FIG. 4, an experiment with a real device was conducted by installing the movable mechanism 2 of the device 1 in a human leg. A product of Harmonic Drive Systems Inc. with a reduction ratio of 50 was used as a motor. A rated torque of the motor was 5.4 Nm and a maximum torque was 24 Nm. In addition, a torque sensor was built in the speed reducer, which detects interaction force generated between the wearer and the device.

Motion of the device 1, which has already been described, will be summarized with reference to FIG. 5. The computer 3 determines a command voltage from torque calculated by the phase oscillator, gives the voltage from D/A converter via the driver to the motor 21, and drives an arm (corresponding to the link 13 of FIG. 4). Then, a joint angle of the arm after being driven is measured with the encoder 23, and the interaction force is measured with the torque sensor 22. The joint angle and the interaction force are incorporated into the computer 3 via the amplifier and the driver from A/D converter and the counter, respectively. Based on these pieces of information, torque of the following device is calculated by the phase oscillator.

A test subject performs movement in a state of sitting on a stand with a level at which a leg does not touch a ground. The test subject fixes a cervix of a right leg to the link 13 of the device with a band for fixing (installation tool 16), and causes movements of the device and the test subject to interact. The link 12 was fixed so as not to move with respect to the sitting stand (see FIG. 4). Since the test subject was in the state of sitting on a chair and neither the thigh region 101 nor the link 12 moves with respect to the sitting stand, installation of the installation tool 15 illustrated in FIG. 4 was omitted. In addition, in order to evaluate the movement of the test subject at a time of the experiment, surface muscle action potential is measured. Measuring points are five points of a rectus femoris muscle, vastus medialis muscle, and vastus lateralis muscle which are used at a time of knee joint extension, and a biceps femoris muscle and semitendinous muscle which are used for bending the leg.

Figure 11:
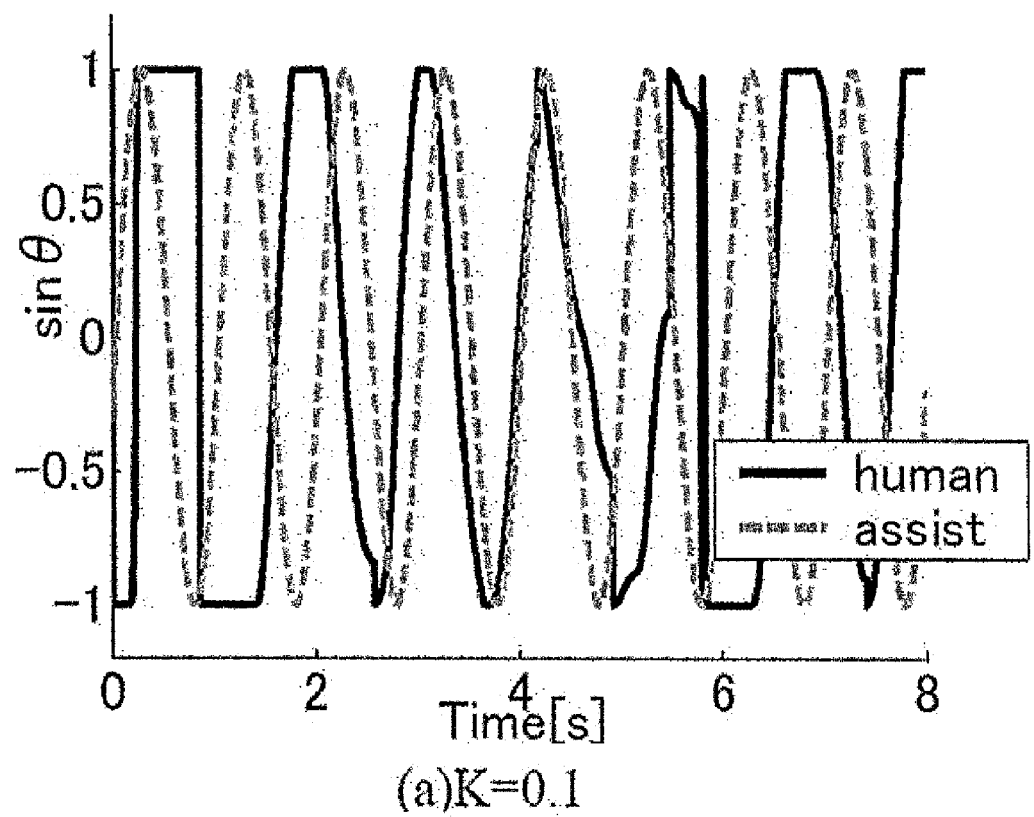
FIG. 11 is a sinusoidal waveform of a phase of a device and a wearer when K=0.1.
Figure 12:
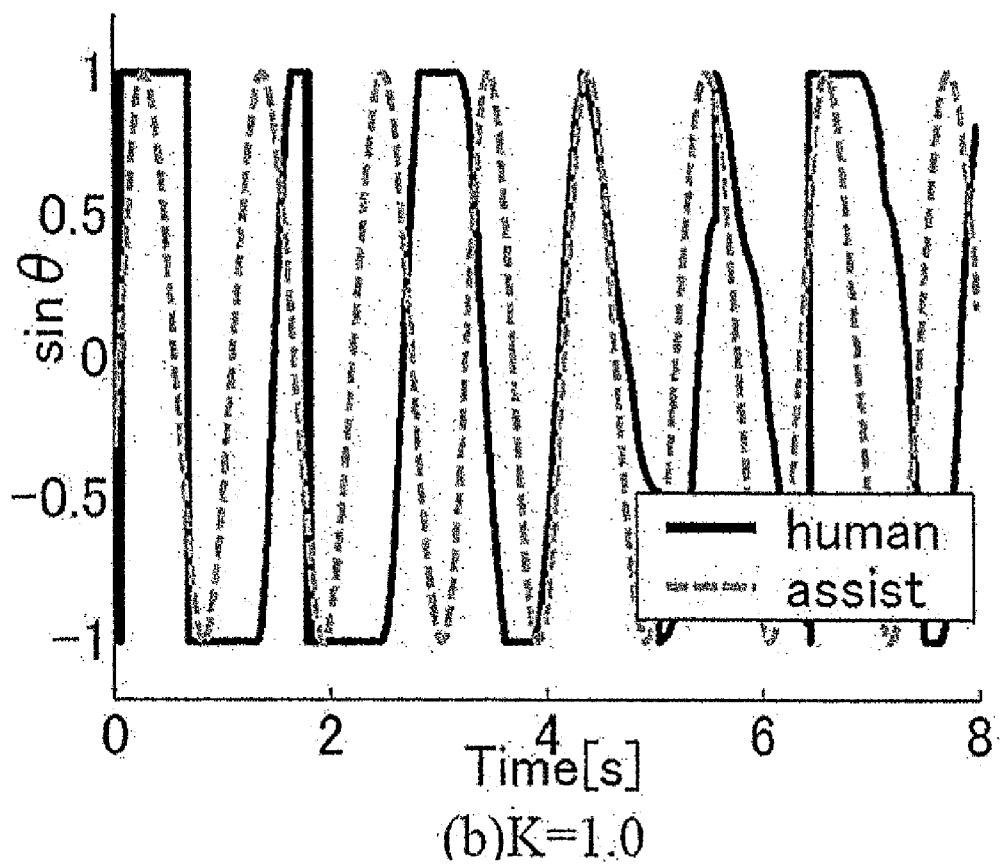
FIG. 12 is a sinusoidal waveform of a phase of the device and the wearer when K=1.0.
Figure 13:
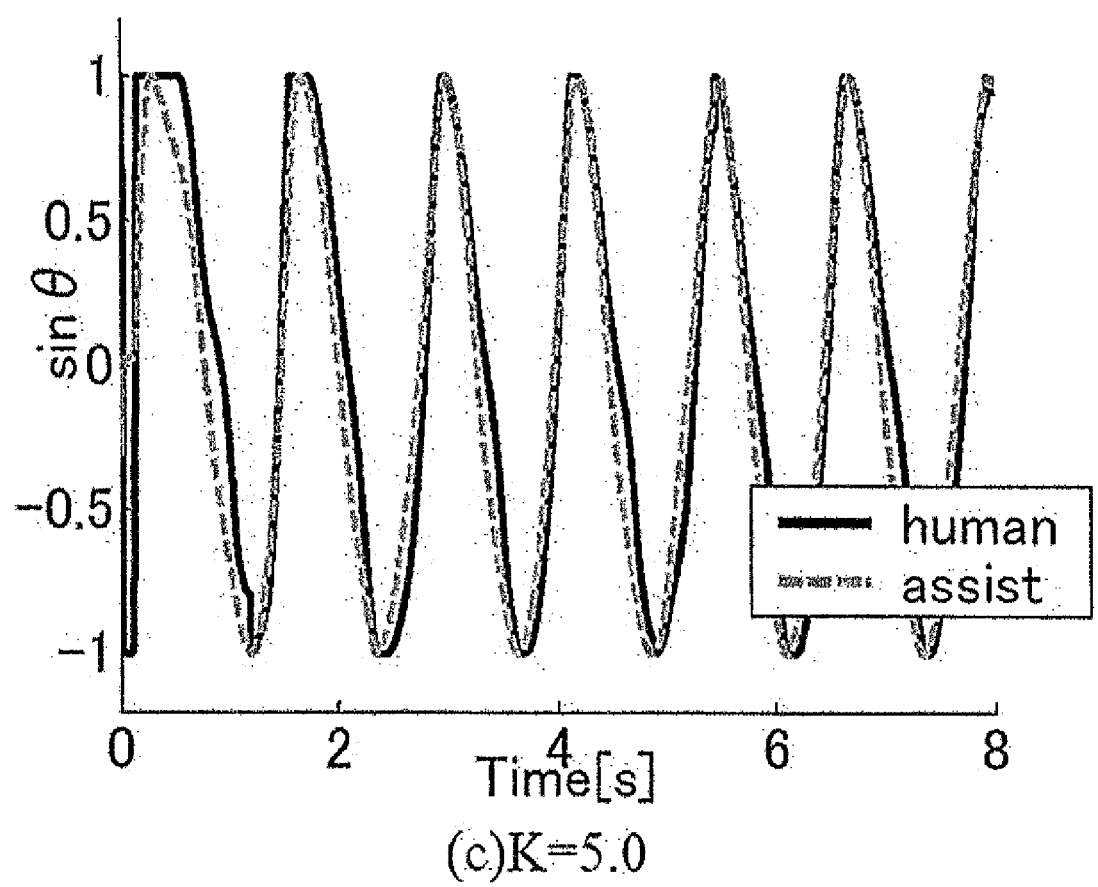
FIG. 13 is a sinusoidal waveform of a phase of the device and the wearer when K=5.0.

In the present experiment, the wearer performs movement at 0.80 Hz, and the interaction with the device was verified. A natural angular frequency $\omega_a$ of the oscillator of the device was set at 5.7 rad/s (frequency of 0.90 Hz), an initial phase $\theta_{a0}$ was set at $0.10\pi$ rad, and amplitude $A_a$ of a torque waveform to output was set at 6.0 Nm. First, FIG. 11, FIG. 12, and FIG. 13 illustrate sinusoidal waveforms of a phase of each oscillator and an estimated phase of the wearer when a synchronization gain K was adjusted at 0.1, 1.0, and 5.0, respectively. It is observed from each Fig. that a frequency of the device approaches a natural frequency of the device as the synchronization gain decreases, and that the frequency of the device approaches the wearer's natural frequency conversely as the synchronization gain increases. In addition, the estimated phase of the wearer is easily distorted when K is 0.1 and 1.0. This is considered because a case where the device becomes assistance to the wearer's motion and a case where the device conversely inhibits the wearer's motion are intermingled due to a difference in the frequency of motion between the device and the wearer, and accordingly an estimated value of the wearer's torque easily varies, and an estimated value of the wearer's phase that is determined based on the estimated value of the wearer's torque also varies.

(Verification of Assisting Effect)

In order to verify an assisting effect of the device with the synchronization gain set at K=5.0 on the movement of the wearer, maximum voluntary contraction strength (% MVC) was derived using a root mean square (RMS) of the measured muscle action potential. For verification, as illustrated in FIG. 4, a muscle action potential sensor 201 for measuring muscle action potential was attached to the wearer. A muscle action potential measuring instrument was connected to a tip of wiring of the muscle action potential sensor 201, although not illustrated. The maximum voluntary contraction strength was calculated by dividing an average of the RMS value during 10 seconds by RMS at a time of maximum voluntary contraction. Table 1 illustrates the maximum voluntary contraction strength of five muscles measured in a case of performing movement only by the wearer and in a case where an interaction is performed with the device.

TABLE 1

|  | Only Wearer | When The Device is Installed |
|---|---|---|
| Rectus Femoris Muscle | 29.8 | 22.9 |
| Vastus Lateralis Muscle | 21.8 | 12.9 |
| Rectus Femoris Muscle | 40.6 | 30.6 |
| Biceps Femoris Muscle | 25.1 | 24.3 |
| Semitendinous Muscle | 17.6 | 29.8 |

It is observed from Table 1 that the maximum voluntary contraction strength in a case of performing an interaction with the device has a tendency to decrease compared with a case of movement only by the wearer. Particularly, decrease of about 10% is observed in the maximum voluntary contraction strength of the rectus femoris muscle, vastus medialis muscle, and vastus lateralis muscle used for extension. This shows that the device that undergoes synchronization based control in accordance with the present embodiment assists the wearer's motion effectively. In contrast, regarding the semitendinous muscle, it is observed that the maximum voluntary contraction strength rises when the interaction is performed with the device. This is considered because force that pulls the wearer's leg in a pivot direction of the joint on a motor side is applied by a fixing band for fixing at a time of extension of the knee joint.

INDUSTRIAL APPLICABILITY

The motion assist device and the synchronization based control method for the motion assist device according to the present invention can generate the motion pattern for the motion assist device with the arbitrary phase difference generated with respect to the wearer's motion, thereby allowing appropriate assistance to the wearer's motion even when assisting a motion of an articulated object such as a leg. The present device and the synchronization based control method therefor can adjust synchronism of the device with respect to a human by appropriately setting the phase difference and the synchronization gain. Therefore, the present device and the synchronization based control method therefor can be used for assistance to a movement in which the device synchronizes its motion timing with that of a human by increasing synchronism. Moreover, the present device and the synchronization based control method therefor can be used for movement teaching rehabilitation in which the device hauls a human by decreasing synchronism.

EXPLANATIONS OF LETTERS OR NUMERALS

Numerals mean as follows. 1: motion assist device, 2: movable mechanism, 3: computer, 4: interface circuit, 11: joint, 12,13: link, 15,16: installation tool, 21: actuator (motor), 22: interaction force detection sensor (torque sensor), 23: joint angle sensor (encoder), 31: phase acquisition unit, 32: phase estimation unit, 33: target value calculation unit, 34: drive control unit, 100: human body, 101: thigh region, 102: knee joint, 103: leg region, 201: muscle action potential sensor, S1: interaction force detection step, S2: joint angle detection step, S3: torque estimation step, S4: torque amplitude calculation step, S5: y-coordinate calculation step, S6: x-coordinate calculation step, S7: phase transformation step, S8: target value calculation step, S9: drive control step

What is claimed is:

1. A motion assist device comprising:
 a joint configured for corresponding to a wearer's bent movable region;
 a link connected to the joint, the link being installed for the wearer;
 an actuator configured to drive a motion of the joint;
 a phase acquisition unit configured to acquire a phase $\theta'_h$ of a motion of the wearer's bent movable region;
 a target value calculation unit configured to calculate a target value of motion of the joint for synchronizing the motion for the wearer's bent movable region and the motion of the joint while maintaining a preset target phase difference based on a phase oscillator model whose the phase $\theta'_h$ of the motion of the bent movable region acquired by the phase acquisition unit is an input oscillation; and
 a drive control unit configured to drive the actuator based on the target value of motion calculated by the target value calculation unit.

2. The motion assist device according to claim 1, wherein the phase acquisition unit includes
 an interaction force detection sensor configured to detect interaction force of the motion for the wearer's bent movable region and the motion of the joint;
 a joint angle sensor configured to detect a joint angle of the joint; and
 a phase estimation unit configured to estimate the phase $\theta'_h$ of the motion for the wearer's bent movable region based on the interaction force detected by the interaction force detection sensor and the joint angle detected by the joint angle sensor.

3. The motion assist device according to claim 2, wherein the phase estimation unit
 estimates torque $\tau'_h$ for the wearers bent movable region by the following Equation (1) from interaction force $\lambda$ detected by the interaction force detection sensor and the joint angle q detected by the joint angle sensor;

$$\tau'_h = M_h \ddot{q} + G_h q \lambda \qquad (1)$$

wherein in Equation (1), $M_h$ and $G_h$ denote a human inertia term and a gravity term; respectively
 estimates maximum torque $\tau'_{h\_max}$ and minimum torque $\tau'_{h\_min}$ of a human in motion by further using the Equation (1), substitutes $\tau'_{h\_max}$ and $\tau'_{h\_min}$ into the following Equation (2), and calculates amplitude $A'_h$ of the estimated torque $\tau'_h$;

$$A'_h = \frac{\tau'_{h\_max} - \tau'_{h\_min}}{2} \qquad (2)$$

calculates a y-coordinate of a phase angle on polar coordinates by the following Equation (3) from the torque $\tau'_h$ and the amplitude $A'_h$;

$$y = \frac{\tau'_h - (A'_h + \tau'_{h\_min})}{A'_h} \qquad (3)$$

calculates an x-coordinate by the following Equation (4) from the Pythagorean theorem;

$$\dot{y} \geq 0 \quad \dot{y} < 0$$

$$x = \sqrt{1-y^2} \quad x = -\sqrt{1-y^2} \qquad (4)$$

performs polar coordinate transformation by the following Equation (5); and $$\theta'_h = \alpha \tan 2(y,x)(-\pi \leq \theta'_h \leq \pi) \qquad (5)$$

estimates the phase $\theta'_h$ of the motion for the wearer's bent movable region.

4. The motion assist device according to claim 1, wherein the target value calculation unit calculate driving torque of the joint by Output of Equation (7) as the target value of motion based on a mathematical model composed of a phase oscillator that has relationships of the following Equation (6) and Equation (7)

$$\dot{\theta}_\alpha = \omega_\alpha K \sin(\theta'_h - \theta_\alpha + \theta_d) \qquad (6)$$

$$\text{Output} = A_\alpha \sin \theta_\alpha - A_\alpha \sin \theta_{\alpha 0} \qquad (7)$$

wherein in Equation (6), $\omega_\alpha$, $\theta_\alpha$, and K denote a natural frequency, a phase angle, and a synchronization gain of the joint, respectively, and $\theta_d$ denotes the target phase difference, and in Equation (7), $A_\alpha$ and $\theta_{\alpha 0}$ denote amplitude of an Output waveform and an initial phase of an oscillator, respectively, and a second term of right side in Equation (7) is a term for setting an initial value of the Output waveform at 0.

5. The motion assist device according to claim 1, wherein the drive control unit performs feedback control of the actuator based on the target value of motion calculated by the target value calculation unit.

6. A synchronization based control method for a motion assist device, the motion assist device including
 a joint configured for corresponding to a wearer's bent movable region,
 a link connected to the joint, the link being installed for the wearer,
 an actuator configured to drive a motion of the joint, and assisting a motion for the wearer,
 the control method comprising:
 a phase acquisition step of acquiring a phase $\theta'_h$ of a motion for the wearer's bent movable region;
 a target value calculation step of calculating a target value of motion for the joint for synchronizing the motion of the wearer's bent movable region and the motion of the joint while maintaining a preset target phase difference based on a phase oscillator model with the phase $\theta'_h$ of the motion of the bent movable region acquired in the phase acquisition step being an input oscillation; and
 drive control step of driving the actuator based on the target value of motion calculated in the target value calculation step.

7. The synchronization based control method for the motion assist device according to claim 6, wherein the phase acquisition step includes
 an interaction force detection step of detecting interaction force of the motion of the wearer's bent movable region and the motion of the joint;

a joint angle detection step of detecting a joint angle of the joint; and a phase estimation step of estimating the phase $\theta'_h$ of the motion for the wearers bent movable region based on the interaction force detected in the interaction force detection step and the joint angle detected in the joint angle detection step.

8. The synchronization based control method for the motion assist device according to claim 7, wherein the phase estimation step includes a torque estimation step of estimating torque $\tau'_h$ for the wearer's bent movable region by the following Equation (1) from interaction force $\lambda$ detected in the interaction force detection step and the joint angle q detected in the joint angle detection step, $$\tau'_h = M_h \ddot{q} + G_h q + \lambda \tag{1}$$

wherein in Equation (1), $M_h$ and $G_h$, denote a human inertia term and a gravity term, respectively a torque amplitude calculation step of estimating maximum torque $\tau'_{h\_max}$ and minimum torque $\tau'_{h\_min}$ of a human in motion by further using the Equation (1); substituting $\tau'_{h\_max}$ and $\tau'_{h\_min}$ into the following Equation (2), and calculating amplitude $A'_h$ of the estimated torque $\tau'_h$;

$$A'_h = \frac{\tau'_{h\_max} - \tau'_{h\_min}}{2} \tag{2}$$

a y-coordinate calculation step of calculating a y-coordinate of a phase angle on polar coordinates by the following Equation (3) from the torque $\tau'_h$ and the amplitude $A'_h$;

$$y = \frac{\tau'_h - (A'_h + \tau'_{h\_min})}{A'_h} \tag{3}$$

an x-coordinate calculation step of calculating an x coordinate by the following Equation (4) from the Pythagorean theorem; and

•$\dot{y} \geq 0$  •$\dot{y} < 0$ $$x = \sqrt{1-y^2} \quad x = -\sqrt{1-y^2} \tag{4}$$

a phase transformation step of performing polar coordinate transformation by the following Equation (5), and calculating the phase $\theta'_h$ of the motion for the wearer's bent movable region $$\theta'h = \alpha \tan 2(y,x)(-\pi \leq \theta'_h \leq \pi) \tag{5}$$

9. The synchronization based control method for the motion assist device according to claim 6, wherein, in the target value calculation step, driving torque of the joint is calculated by Output of Equation (7) as the target value of motion based on a mathematical model composed of a phase oscillator that has relationships of the following Equation (6) and Equation (7)

$$\dot{\theta}_\alpha = \omega_\alpha + K \sin(\theta'_h - \theta_\alpha + \theta_d) \tag{6}$$

$$\text{Output} = A_\alpha \sin \theta_\alpha - A_\alpha \sin \theta_{\alpha 0} \tag{7}$$

Equation (6), $\omega_a$, $\theta_a$, and K denote a natural frequency, phase angle, and synchronization gain of the joint, respectively, and $\theta_d$ denotes the target phase difference, and in Equation (7), $A_a$ and $\theta_{a0}$ denote amplitude of an Output waveform and an initial phase of an oscillator, respectively, and a second term of a right side in Equation (7) is a term for setting an initial value of the Output waveform at 0.

10. The synchronization based control method for the motion assist device according to claim 6, wherein, in the drive control step, feedback control of the actuator is performed based on the target value of motion calculated by the target value calculation unit.

* * * * *